(12) United States Patent
Dietz et al.

(10) Patent No.: US 10,279,193 B2
(45) Date of Patent: May 7, 2019

(54) SPACE, LUMINOUS CEILING SYSTEM AND METHOD FOR CONDUCTING PHOTODYNAMIC THERAPY

(71) Applicant: SWISS RED AG, Murten (CH)

(72) Inventors: John Dietz, Bonn (DE); Uwe Reinhold, Bonn (DE)

(73) Assignee: SWISS RED AG, Murten (CH)

( * ) Notice: Subject to any disclaimer, the term of this patent is extended or adjusted under 35 U.S.C. 154(b) by 32 days.

(21) Appl. No.: 15/035,930

(22) PCT Filed: Nov. 11, 2014

(86) PCT No.: PCT/EP2014/074275
§ 371 (c)(1),
(2) Date: May 11, 2016

(87) PCT Pub. No.: WO2015/071262
PCT Pub. Date: May 21, 2015

(65) Prior Publication Data
US 2016/0263392 A1 Sep. 15, 2016

(30) Foreign Application Priority Data

Nov. 13, 2013 (DE) .................. 20 2013 105 127 U

(51) Int. Cl.
*A61N 5/06* (2006.01)

(52) U.S. Cl.
CPC ........... *A61N 5/062* (2013.01); *A61N 5/0616* (2013.01); *A61N 2005/0636* (2013.01); *A61N 2005/0654* (2013.01); *A61N 2005/0663* (2013.01); *A61N 2005/0665* (2013.01)

(58) Field of Classification Search
USPC .................... 606/2–19; 607/86–94
See application file for complete search history.

(56) References Cited

U.S. PATENT DOCUMENTS 6,135,117 A * 10/2000 Campbell ............ A61N 5/0618
128/898
2005/0080465 A1* 4/2005 Zelickson ............ A61N 5/0616
607/88

(Continued)

FOREIGN PATENT DOCUMENTS

| DE | 20 2013 003573 U1 | 7/2013 |
|---|---|---|
| EP | 1 147 785 A2 | 10/2001 |
| WO | WO 2004/080291 A2 | 9/2004 |

OTHER PUBLICATIONS

Bozja, J. et al., "Porphyrin-Based, Light-Activated Antimicrobial Materials," J or Polymer Science Part A: Polymer Chemistry, John Wiley & Sons, Inc., US, Jan. 2003, vol. 41, pp. 2297-2303.

(Continued)

*Primary Examiner* — Carl H Layno
*Assistant Examiner* — Dacheng Xie
(74) *Attorney, Agent, or Firm* — Pauley Erickson & Kottis

(57) ABSTRACT

A space for conducting photodynamic therapy (PDT) for treatment of skin diseases, especially for treatment of superficial skin tumors such as actinic keratoses, basal cell carcinomas, and initial carcinomas, wherein an active ingredient is applied to a skin area to be treated in order to form porphyrins and irradiation with light is conducted to form singlet oxygen based on the porphyrins in order to destroy diseased skin cells, wherein the space has side walls, a ceiling, and a floor, as well as at least two lighting fixtures, which are separated from one another by at least 50 cm and illuminate at least a subregion of the space, wherein there is an illuminance of at least 8,000 lux at every point in the subregion and the subregion has horizontal dimensions of at (Continued)

least 1 m² and a vertical height of at least 40 cm. This invention also relates to a luminous ceiling system and method for conducting PDT.

14 Claims, 1 Drawing Sheet

(56) References Cited

U.S. PATENT DOCUMENTS

| | | | | |
|---|---|---|---|---|
| 2008/0312721 | A1* | 12/2008 | Lemieux | A61N 5/0614 607/91 |
| 2011/0117202 | A1* | 5/2011 | Bourke, Jr. | H05B 41/2806 424/490 |
| 2012/0238939 | A1* | 9/2012 | Gerstenmeier | A61N 5/0616 604/20 |
| 2013/0268033 | A1* | 10/2013 | Maass | A61N 5/0618 607/88 |

OTHER PUBLICATIONS

Bhasin, H. et al., "Ferrochelatase, a novel target for photodynamic therapy of cancer," Oncology Reports, Spandidos Publication, GR, Nov. 1999, vol. 6, No. 6, pp. 1439-1442.

European Patent Office, Form PCT/ISA/210, International Search Report for International Patent Application PCT/EP2014/074275, dated Feb. 24, 2015 (3 pages).

* cited by examiner

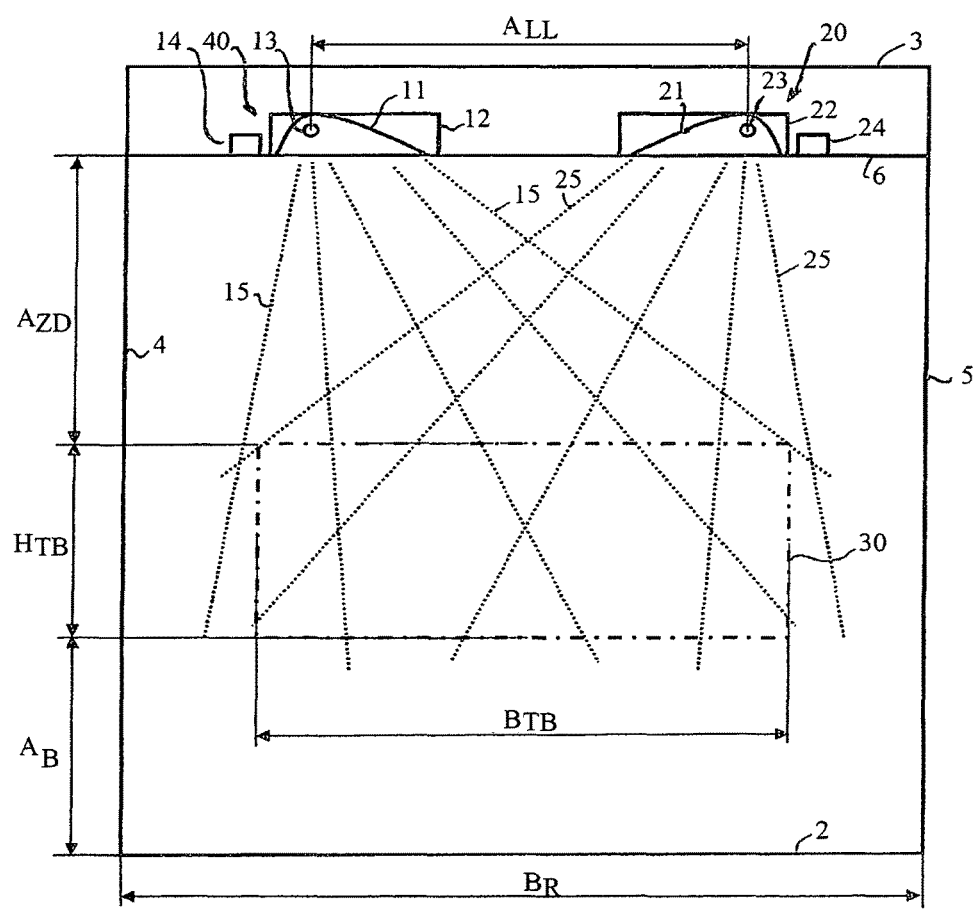

SPACE, LUMINOUS CEILING SYSTEM AND METHOD FOR CONDUCTING PHOTODYNAMIC THERAPY

BACKGROUND OF THE INVENTION

Field of the Invention

This invention relates to a space, luminous ceiling system, and a method for conducting photodynamic therapy (PDT).

Discussion of Related Art

One objective of photodynamic therapy (PDT) is the oxygen-dependent destruction of skin tumor cells, which occurs after a previous photosensitization and illumination of a suitable wavelength. The destruction occurs selectively; the PDT destroys tumor cells and their precursors, but not the healthy cells.

In PDT, a cream containing, for example, the active ingredient 5-alpha-aminolevulinic acid (ALA) as a photosensitizer is applied to the skin area with the diseased tissue to produce light-sensitive porphyrins, in particular protoporphyrin 9 (PPIX). The active ingredient ALA and thus the porphyrins that are formed from it intensively accumulate in inflammation-altered tissue and malignant tumors. This makes it possible to selectively treat and destroy pathologically altered skin structures. Due to the irradiation, the porphyrins absorb energy and transmit this to the oxygen in the cells. Because of the energy absorption, the "normal" triplet oxygen transitions into an excited state (singlet oxygen). These oxygen radicals destroy the affected cells. The local action of the release of oxygen radicals prevents further damage to healthy cells.

Basically, it is possible to distinguish between closed PDT and open daylight PDT. In closed PDT, cream is applied to the skin area to be treated and then an opaque dressing (for example aluminum foil) is applied. After three or four hours of application time, the dressing is removed. During this time, the active ingredient has accumulated in the diseased cells, while the healthy cells have absorbed hardly any of it. The photoactive porphyrins form in the diseased cells. The affected area is then intensively irradiated for about 10 minutes with a special PDT lamp. The lighting intensity in this case is very high and despite the relatively short illumination times, results in a light dosage of up to 200 J/cm$^2$. In PDT lamps with a narrower light spectrum, the required light dosage can be significantly reduced while achieving the same therapeutic effect. In this case as well, though, the values for the light dosage are about 37 J/cm$^2$.

The irradiation by the PDT lamp in closed PDT can sometimes cause severe pain. In connection with closed PDT, it is therefore known to administer painkillers before the irradiation.

By contrast with closed PDT, so-called daylight PDT is painless. In daylight PDT, the active ingredient ALA is likewise applied, but the wait time is only about 30 minutes and then the cream-treated skin area is illuminated with natural daylight for a period of 1.5-3 hours. With daylight PDT, an irradiation energy of 10 J/cm$^2$ is sufficient.

With daylight PDT, the exposure power or exposure level depends on the geographical location, the geodetic height, the position of the sun, the time of year, and the current weather. For example when there is unfavorable weather during wintertime, it may not be possible to perform daylight PDT for several weeks since the daylight is too weak to sufficiently excite the porphyrins in order permit the generation of singlet oxygen for destroying the tumor cells. On a cloudy winter day, for example, the exposure level does not exceed 4000 lux.

SUMMARY OF THE INVENTION

Thus, one object of this invention is to provide a device and method that can be used to conduct photodynamic therapy for treatment of skin diseases, wherein the PDT should be as painless as possible and should be possible to perform at any time without time restrictions.

The above and other objects of this invention are attained with exemplary embodiments of this invention as described in this specification and in the claims, particularly the use of a space and luminous ceiling system for the treatment of superficial skin tumors.

The space according to this invention is used for conducting PDT, which can be used to treat skin diseases. In this case, the focus is on the treatment of superficial skin tumors. Examples of such skin tumors include actinic keratosis, basal cell carcinomas, and initial carcinomas.

The space according to this invention has side walls, a ceiling, a floor, and at least two lighting fixtures, which are spaced at least 50 centimeters apart from each other. According to this invention, the at least two lighting fixtures illuminate a subregion of the space and there is an exposure level of at least 8,000 lux at every point in the subregion and the subregion has horizontal dimensions of at least one square meter (1 m$^2$) and a vertical height of at least 40 centimeters (40 cm).

In one exemplary embodiment, the minimum exposure level at every point in the subregion is 10,000, 12,000, or even 15,000 lux. The horizontal dimensions (maximum surface area of the subregion in a horizontal plan) can be greater than 2, 4, or 8 square meters. The vertical height of the subregion (maximum vertical height) can be up to 50, 70, or 100 centimeters. The distance between two lighting fixtures can also be greater than 70 or 100 centimeters, one important factor is the distance between any two lighting fixtures, not necessarily the distance between adjacent lighting fixtures. A minimum distance between adjacent lighting fixtures can be 20, 30, or 40 centimeters.

In one embodiment of this invention, the exposure level inside the subregion only assumes values that are less than 30,000 lux. The maximum exposure level can also be only 25,000 or even 20,000 lux.

If after the photosensitizer is applied to the skin area that is to be irradiated, a patient sits or lies in the space according to this invention so that the affected skin area is positioned within the subregion of the space and is irradiated with the light of the at least two lighting fixtures for approximately 1.5-3 hours, then it is possible to achieve the same therapeutic effects as with classic closed PDT. But a great difference is that during the irradiation in the space according to this invention, the patient does not feel any pain. In comparison to daylight PDT, a significant difference is that the PDT is totally independent of parameters that cannot be influenced (for example weather and time of year). Instead, the exposure level or lighting intensity can be adjusted accurately and the PDT can be carried out at any time and in any place under the same boundary conditions. With a PDT of this kind, a light dosage of at least 10 J/cm$^2$ can be achieved.

Another advantage is that the patient can move freely in the space during the irradiation time, as long as the skin area to be treated remains in the subregion and is exposed to the light of the lighting fixtures.

In one exemplary embodiment of this invention, within the subregion, the illuminance does not deviate by more than 50 percent from the maximum value in the subregion. If, for example, a maximum value of 22,000 lux is achieved at one point in the subregion, then at least 11,000 lux is required in every other point in the subregion. Consequently, within the entire subregion, an irradiation intensity prevails at approximately the same level that on the one hand, does not cause any pain, but on the other hand, also permits the formation of singlet oxygen to a sufficient degree by the excited porphyrins.

Preferably, the lighting fixtures are installed on the ceiling or in a false ceiling of the space. As is also the case with daylight PDT, the irradiation is primarily carried out from above. Alternatively or additionally, the lighting fixtures can also be installed in the side wall and on the floor. Optimal results are achieved, however, by lighting fixtures close to the ceiling. The side walls and the floor can be used as reflective surfaces, which can intensify the exposure level in the subregion. The subregion can be situated off-center in the space in order to thus be able, for example, to make better use of the reflections of the side walls in a corner of the space.

A distance between the floor and the ceiling of the space can be between 230 and 350 centimeters. The space according to this invention would thus have a room height that that corresponds to the usual room height in old or new buildings. It would thus be possible to inexpensively convert existing treatment rooms in a dermatology practice into a space according to this invention.

If a false ceiling is provided, then the above-indicated values (230 to 350 cm) refer to the distance between the floor and the false ceiling. At this point, it should be noted that dimensions or features of exemplary embodiments of this invention are optional, not mandatory. Thus the space according to this invention can also have a room height of more than 4 m. In this case, the lighting fixtures may possibly have to be designed differently in order to obtain the required exposure levels.

A distance between the floor and the subregion can total 40 to 120 centimeters (in relation to a lower end of the subregion). For example, assuming there is a vertical height of the subregion of 50 centimeters, a distance between the floor and subregion of one meter, and a ceiling height of 250 centimeters, then this would yield a distance of one meter between the lighting fixtures and the subregion (upper end of the subregion).

One of the lighting fixtures, preferably all of the lighting fixtures, can be a lamp that continuously emits light in the wavelength range from 560 to 660 nm. In other words, the light spectrum of this lamp has no gaps in this wavelength range. In particular, a light with a wavelength of 630 nm (nanometers) is emitted, whose energy is absorbed by the porphyrins. The lamp can also be produced so that it emits more than 75 percent (preferably more than 80 or 90 percent) of its total radiation in this range. Consequently, the radiant energy density of the lamp is relatively low for wavelengths of less than 560 nm and greater than 660 nm. Another preferred lamp emits at least 80% (preferably more than 90%) of its radiant energy in a wavelength range from 600 to 650 nm.

The lighting fixtures can be arranged in two or more parallel rows. For example, it is conceivable for there to be a lighting arrangement that is composed of a total of eight lighting fixtures that are arranged in two rows of four. It is also possible to provide a centrally located lighting fixture around which a number of outer lighting fixtures are arranged, spaced equidistantly apart from it in a concentric circle.

Each lighting fixture can have a reflector, which focuses the light and/or guides it in a particular way in a direction so that the light of several lighting fixtures overlaps in such a way that the subregion is illuminated as well as possible (for example as uniformly as possible in a horizontal plane). Each lighting fixture can have a symmetrical or asymmetrical reflector. An asymmetrical reflector can be oriented so that in a lighting arrangement with a number of lighting fixtures, the asymmetrical reflectors are integrated into a symmetrical overall formation. If there are obstacles (such as ventilation ducts) on the ceiling, then a selection and individual design of the reflectors can be used to achieve an essentially homogeneously illuminated subregion, even if the lighting fixtures are installed on the ceiling in an irregular pattern.

The lighting fixtures can be flush-mounted in a false ceiling. This means that the false ceiling and a lower edge of a reflector essentially lie in the same plane. In order to counteract an excessive temperature increase in the intermediate space between the false ceiling and the ceiling, a cooling device can be provided, for example in the form of a blower.

This invention also presents a luminous ceiling system for a space for conducting photodynamic therapy. The luminous ceiling system has at least two lighting fixtures, preferably more than four lighting fixtures, at least two of which are spaced apart from each other by a distance of more than 50 or even by a distance of more than 80 centimeters. The luminous ceiling system in this case is designed so that for one subregion of the space, it produces an exposure level of at least 8,000 (preferably 12,000) lux, with the subregion being at least 1 m$^2$ (preferably greater than 4 or 6 m$^2$) in size in the horizontal direction and being spaced apart from the luminous ceiling system by at least 100 cm. The luminous ceiling system in this case should be used for treatment of skin diseases, especially for treatment of superficial skin tumors such as actinic keratosis, basal cell carcinomas, and initial carcinomas. It should produce enough radiant energy to permit the production, with the aid of porphyrins, of oxygen radicals (singlet oxygen) in diseased skin cells.

In the method according to this invention for conducting photodynamic therapy (PDT) for treatment of skin diseases, especially for treatment of superficial skin tumors such as actinic keratosis, basal cell carcinomas, and initial carcinomas, wherein an active ingredient is applied to a skin area to be treated in order to form porphyrins and irradiation with light is conducted to form singlet oxygen based on the porphyrins in order to destroy diseased skin cells, wherein the irradiation with light takes place in a space according to this specification and the claims for more than one hour and wherein the irradiation energy amounts to less than 20 J/cm$^2$. Preferably, the irradiation with light takes place in the space as described above in its various embodiments for more than 1.5 hours. The irradiation energy can assume values of less than 15 J/cm$^2$ or even 12 J/cm$^2$.

BRIEF DESCRIPTION OF THE DRAWING

This invention is explained in greater detail in view of an exemplary embodiment shown in FIG. 1 which shows a cross-section taken through a space, which is labeled as a whole with element reference numeral 1.

DETAILED DESCRIPTION OF THE INVENTION

The space 1 has a floor 2, a ceiling 3, and side walls, but only a left side wall 4 and a right side wall 5 are shown in FIG. 1.

Spaced apart from the ceiling 3, a false ceiling 6 extends parallel to it. The distance between the ceiling 3 and false ceiling 6 can, for example, be 20-30 centimeters. A first lighting fixture 10 and a second lighting fixture 20 are mounted in the false ceiling 6. Because the lighting fixtures 10, 20 are embodied as structurally identical and are merely installed in mirror-image fashion, only the first lighting fixture 10 is referred to below. The following statements regarding the first lighting fixture 10 consequently also apply analogously to the second lighting fixture 20.

The first lighting fixture 10, which is embodied here as a surface transmitter, has an asymmetrical reflector 11 that is accommodated in a lighting fixture housing 12. A lamp 13, which the reflector 11 encloses at the top, has a light spectrum with a high radiant energy density in or near 630 nm. To start and/or operate the lamp 13, a ballast 14, which is situated outside the lighting fixture housing 12.

Such an arrangement serves to protect the ballast from excessive heat that is produced in the first lighting fixture 10. The electrical power of the lighting fixture 10 can be 400 Watt and more (for example 500 to 1000 Watt).

The lamp 13 is an essentially cylindrical lamp with a diameter of 2 to 4 centimeters and a length of 15 to 25 centimeters. Consequently, the asymmetrical reflector 11 and the lamp extend into the plane of the drawing with the essentially constant cross-section shown here. The lighting fixture housing 12 is thus the shape of a block. The lighting fixture housing can be square in shape (such as the cross-section of the lighting fixture housing is square when viewed from above or below). The lighting fixture 10 can thus be favorably integrated into existing false ceilings, which usually have a square pattern.

The first lighting fixture 10 emits light, which the depicted light beams 15 are intended to illustrate. These beams 15 overlap with corresponding light beams 25 of the second lighting fixture 20.

Inside the space 1, a subregion can be defined, which is labeled with the reference numeral 30. The subregion 30 has a vertical height $H_{TB}$ and a width $B_{TB}$ in the horizontal direction. A distance from the floor 2 is labeled $A_B$ and a distance from the false ceiling 6 is labeled $A_{ZD}$. For example, if a width of the space $B_R$ is 2.50 m, then in the exemplary embodiment shown here, the subregion 30 is approximately 1.60 m wide ($B_{TB}$=1.6 m). The height $H_{TB}$ is approximately 70 cm, with the distance from the floor $A_B$ being about 80 cm. The distance $A_{ZD}$ between the subregion 30 and the false ceiling 6 measures about 100 cm. A distance $A_{LL}$ between the two lighting fixtures 10, 20 (respectively calculated from the center point of the lamps 13, 23) is approximately 1.3 m.

As explained above, FIG. 1 is a cross-sectional depiction. The subregion 30 thus extends into the plane of the drawing and can, for example, be 3 meters in length. In this case, this would yield a horizontal dimension of 4.80 m² ($B_{TB}$=1.6 m; $B_{TB}$×3 m). Within the subregion 30, there is an exposure level that should be at least greater than 12,000 lux, but less than 30,000 lux at every point of the subregion. In order to also ensure a sufficiently high exposure level in the longitudinal direction of the subregion (such as perpendicular to the plane of the drawing), there are three other lighting fixtures behind the first lighting fixture 10, viewed in the direction of the depiction in FIG. 1. The same applies analogously to the second lighting fixture 20 so that the space 1 is illuminated by a total of eight lighting fixtures, which are arranged one after another in two rows. In this case, not only does the light of two opposing lighting fixtures overlap (like the first and second lighting fixtures 10, 20 shown in FIG. 1), but so does that of lighting fixtures in the same row. The subregion 30, which in this case has a rectangular cross-sectional shape, can differ from a block shape and can, for example, be an ellipsoid.

A preferred distance between two adjacent lighting fixtures in a row is 60 to 65 cm. A preferred distance between the rows is 1.2 to 1.3 m.

If the irradiation as part of photodynamic therapy is then conducted inside the space 1, after a skin area that is irradiated has previously had a cream containing the active ingredient ALA applied to it in order to produce PPIX in diseased skin cells, then the patient sits or lies in the space so that the skin area is positioned in the subregion 30. The light of the lighting fixtures 10, 20 (and other lighting fixtures) at the above-indicated exposure levels sets in motion the desired reactions for the production of the singlet oxygen. But the concentration of PPIX and the concentration of singlet oxygen do not come anywhere near reaching the same values as in conventional PDT.

The invention claimed is:

1. A space (1) for conducting photodynamic therapy (PDT) for treatment of skin diseases, including treatment of superficial skin tumors including actinic keratosis, basal cell carcinomas, and initial carcinomas, wherein an active ingredient is applied to a skin area to be treated to form porphyrins and irradiation with a light is conducted to form singlet oxygen based on the porphyrins to destroy diseased skin cells, the space (1) comprising:
    side walls (4, 5) extending between a ceiling (3) and a floor (2), wherein there is a distance of 230 to 350 cm between the floor (2) and the ceiling (3);
    at least two lighting fixtures (10, 20) configured to emit at least 8,000 lux combined and separated from one another by at least 50 cm, wherein each of the at least two lighting fixtures has a lamp that continuously emits light in a wavelength range from 560 to 660 nm and emits more than 75 percent of a total radiation in this range, and each of the at least two lighting fixtures includes a reflector configured to direct light beams emitted from the at least two lighting fixtures to overlap; and
    an illuminated treatment subregion (30) of the space provided within the overlap of the light beams emitted from the at least two lighting fixtures, the subregion having horizontal dimensions of at least 1 m² and a vertical height of at least 40 cm, wherein there is a distance of 40 to 120 cm between the floor (2) and a lower horizontal dimension of the subregion (30), the subregion includes treatment illuminance of at least 8,000 lux at every point in the subregion, and the treatment illuminance does not deviate by more than 50% from a maximum value within the subregion (30).

2. The space (1) according to claim 1, wherein the illuminance is no greater than 30,000 lux at every point in the subregion (30).

3. The space (1) according to claim 2, wherein the lighting fixtures are installed on the ceiling (3) or in a false ceiling (6).

4. The space (1) according to claim 3, wherein the lighting fixtures (10, 20) are arranged in two or more parallel rows.

5. The space (1) according to claim 4, wherein the lighting fixtures (10, 20) have asymmetrical reflectors (11, 21).

6. The space (1) according to claim 5, wherein the lighting fixtures are flush-mounted in the false ceiling.

7. The space (1) according to claim 6, wherein a cooling device is provided for the lighting fixtures (10, 20).

8. A method for conducting photodynamic therapy (PDT) for treatment of the skin diseases using the space according to claim 1, the method comprising:
   applying the active ingredient to the skin area to be treated to form the porphyrins; and
   irradiating with the light beams to form the singlet oxygen based on the porphyrins in order to destroy the diseased skin cells, wherein the irradiating takes place in the space (1) for more than one hour and with a total irradiation energy amount of less than 20 J/cm$^2$.

9. The method according to claim 8, wherein the irradiating is carried out in the space with the illuminance being no greater than 30,000 lux at every point in the subregion (30), for more than 1.5 hours and the total irradiation energy amount is less than 15 J/cm$^2$.

10. The method according to claim 8, wherein the treatment is for actinic keratosis, basal cell carcinomas, or initial carcinomas.

11. The space (1) according to claim 1, wherein the lighting fixtures are installed on the ceiling (3) or in a false ceiling (6).

12. The space (1) according to claim 1, wherein the lighting fixtures (10, 20) are arranged in two or more parallel rows.

13. The space (1) according to claim 1, wherein the lighting fixtures (10, 20) have asymmetrical reflectors (11, 21).

14. The space (1) according to claim 1, wherein a cooling device is provided for the lighting fixtures (10, 20).

* * * * *